United States Patent [19]

Hyoda et al.

[11] Patent Number: 6,156,906
[45] Date of Patent: Dec. 5, 2000

[54] PROCESS FOR THE PREPARATION OF 5,5'-BI-1H-TETRAZOLE SALT

[75] Inventors: Shunji Hyoda; Masaharu Kita; Hirotoshi Sawada; Shuichi Nemugaki; Takahiro Ueta; Kohki Satoh, all of Sakaide; Sumio Otsuka, Takamatsu; Yoshitaka Miyawaki, Takamatsu; Hiroshi Taniguchi, Takamatsu, all of Japan

[73] Assignees: Japan Hydrazine Co., Inc.; Masuda Chemical Industry Co., LTD., both of Tokyo, Japan

[21] Appl. No.: 09/374,949

[22] Filed: Aug. 16, 1999

[51] Int. Cl.$^7$ .................. C07D 257/04; C07D 403/04
[52] U.S. Cl. ............................................. 548/250
[58] Field of Search ............................................. 548/250

[56] References Cited

FOREIGN PATENT DOCUMENTS 952 811  11/1956  Germany .
952811   11/1956  Germany .

OTHER PUBLICATIONS

Fred Einberg, "Preparatioon of 5–Dinitromethyletrazole from Salts of Dinitroacetonitrile", Journal of Organic Chemistry, vol. 29, –1964, pp. 2021–2024, XP002135258. American Chemical Society. Easton., US ISSN: 0022–3263, p. 2023, left column.

*Primary Examiner*—Joseph McKane
*Assistant Examiner*—Jane C. Oswecki
*Attorney, Agent, or Firm*—Fulbright & Jaworski L.L.P.

[57] ABSTRACT

A process for the preparation of a 5,5'-bi-1H-tetrazole diammonium salt by dropwisely adding the aqueous hydrogen peroxide to which a small amount of weakly acidic substance has been added, to a starting aqueous solution containing hydrogen cyanide or sodium cyanide or potassium cyanide, sodium azide and a catalytic amount of copper sulfate preferably at a low temperature to maintain the pH of the reaction solution over a range of from 5 to 6, heating the reaction solution to effect the oxidation and cyclization reaction, reacting the reaction product with ammonium chloride or an aqueous solution thereof, and recovering the formed ammonium salt in the form of sparingly soluble crystals. The desired product is obtained in a high yield and in a high purity from the starting materials which are cheaply available and are easy to handle through a decreased number of steps, i.e., through a one-pot reaction without requiring cumbersome after-treatment.

12 Claims, No Drawings

PROCESS FOR THE PREPARATION OF 5,5'-BI-1H-TETRAZOLE SALT

BACKGROUND OF THE INVENTION

1. Field of the Invention

The present invention relates to a process for the preparation of a 5,5'-bi-1H-tetrazole diammonium salt that is useful as a lowly toxic and easy-to-handle gas-generating agent for air bags and as a high molecular foaming agent.

2. Description of the Prior Art

A 5,5'-bi-1H-tetrazole (BHT) and its salts have a chemical structure represented by the following formula (1),

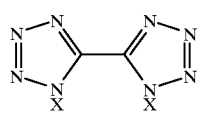

(1)

wherein X is a hydrogen atom or a pair of cations.

There have been known the following four methods of synthesis.

(Prior Art 1, Chemical Abstracts Vol. 31, 4985)

This literature teaches the synthesis of BHT by the reaction expressed by the following formula (2),

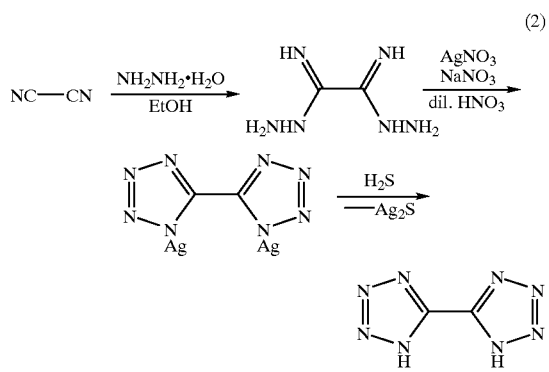

(2)

(Prior Art 2, Friederich DE 952,811, 1956)

This literature discloses a method for the preparation of a bistetrazole by reacting a mole of sodium azide or hydrogen azide with 2 moles of sodium cyanide or hydrogen cyanide in the presence of a small amount of copper salt, and teaches, in the working examples, the recovery of the bistetrazole (BHT) in the form of a bisodium salt (BHT.2Na) by condensing the solution after the reaction.

This reaction is expressed by the following formula (3),

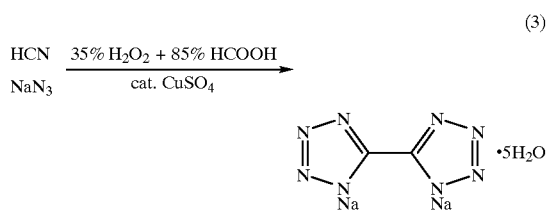

(3)

(Prior Art 3, Friederich DE 952,811, 1956, U.S. Pat. No. 2,710,297, 1955)

This is the same literature as the one quoted above, and teaches the synthesis of the BHT.2Na by the reaction in accordance with the following formula (4),

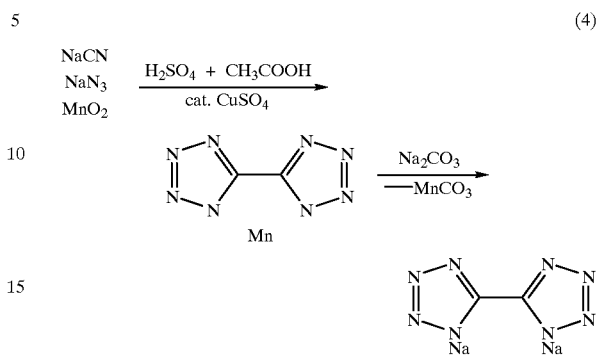

(4)

(Prior Art 4, F. Einberg, J. Org. Chem., 29, (1954) 2021)

This literature discloses the synthesis of a 5,5'-bi-1H-tetrazole diammonium salt (BHT·2NH$_3$) by the reaction expressed by the following formula (5),

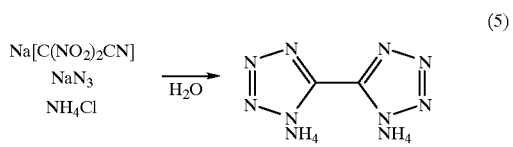

(5)

The prior art 1 teaches the process for obtaining the 5,5'-bi-1H-tetrazole by separating a 5,5'-bi-1H-tetrazole silver salt through the step of forming an azide of an oxalic acid dihydrazide which is a reaction product of a dicyan and a hydrated hydrazine, reacting the 5,5'-bi-1H-tetrazole silver salt with hydrogen sulfide to move it in the form of a silver sulfide. However, this process involves complex steps and requires the use of expensive silver salt and hydrogen sulfide which is toxic.

The prior art 2 teaches the process for synthesizing and isolating the 5,5'-bi-1H-tetrazole disodium salt by using hydrogen cyanide and sodium azide as starting materials. Since the 5,5'-bi-1H-tetrazole disodium salt is soluble in water, it becomes necessary to conduct the step of after-treatment such as condensation for isolating the 5,5'-bi-1H-tetrazole disodium salt from an aqueous solution thereof. Though there has been described that the 5,5'-bi-1H-tetrazole disodium salt is isolated from the aqueous solution through the after-treatment such as condensation, there is no description related to the yields and properties of the isolated compound. The present inventors have conducted trace experiment of Examples of the prior art 2 to find that the yield was as very low as about 30%.

The prior art 3 synthesizes the 5,5'-bi-1H-tetrazole disodium salt by using sodium cyanide, sodium azide and manganese dioxide as an oxidizing agent. However, use of manganese dioxide as an oxidizing agent requires cumbersome after-treatment for removing manganese dioxide.

The prior art 4 uses sodium dinitroacetonitrile, sodium azide and ammonium chloride as starting materials to isolate the 5,5'-bi-1H-tetrazole diammonium salt. However, the reaction time is long, the yield is low and, besides, the sodium dinitroacetonitrile which is the starting material is not easily available.

Though this can be said for known methods as a whole, when dicyan is used as a starting material, it becomes necessary to use the reactor for synthesizing dicyan in addition to the reactor for the 5,5'-bi-1H-tetrazole diammonium salt, causing the reaction steps and the reaction apparatus to become complex.

When the sodium cyanide or hydrogen cyanide is used as a starting material, furthermore, an oxidizing agent is necessary. When a metal salt is used as the oxidizing agent, the reaction intermediate product, i.e., 5,5'-bi-1H-tetrazole metal salt is isolated from the reaction solution and is decomposed arousing, however, a problem of lengthy and complex reaction operation. Besides, use of a heavy metal in the reaction system requires the after-treatment for its removal, which is a serious problem.

In this sense, the method which uses hydrogen peroxide as an oxidizing agent is advantageous but still offers a low yield due to the side reaction of cyan and leaves much room for improvement.

In order to isolate the 5,5'-bi-1H-tetrazole or the 5,5'-bi-1H-tetrazole disodium salt soluble in water, furthermore, the operation such as condensation is required, causing an increase in the number of the steps. Besides, the yield is not satisfactory.

OBJECTS AND SUMMARY OF THE INVENTION

The object of the present invention therefore is to provide a process for the preparation of a 5,5'-bi-1H-tetrazole diammonium salt from the inexpensive and easy-to-handle starting materials through a decreased number of steps, i.e., through the one-pot reaction without requiring cumbersome after-treatment yet maintaining a high yield and a high purity.

According to the present invention, there is provided a process for the preparation of a 5,5'-bi-1H-tetrazole diammonium salt by dropwisely adding the aqueous hydrogen peroxide to which a small amount of weakly acidic substance has been added, to a starting aqueous solution containing hydrogen cyanide, sodium azide and a catalytic amount of copper sulfate preferably at a low temperature to maintain the pH of the reaction solution over a range of from 5 to 6, heating the reaction solution to effect the oxidation and cyclization reaction, reacting the reaction product with ammonium chloride or an aqueous solution thereof, and recovering the formed ammonium salt in the form of sparingly soluble crystals.

DETAILED DESCRIPTION OF THE INVENTION

A process for the preparation of a 5,5'-bi-1H-tetrazole diammonium salt (BHT.2NH$_3$) according to the present invention has a feature in the combination of:

i) preparing a starting aqueous solution containing hydrogen cyanide, sodium azide and a catalytic amount of copper sulfate preferably at a low temperature;
ii) dropwisely adding the aqueous hydrogen peroxide to which a small amount of weakly acidic substance has been added, to the starting aqueous solution to maintain the pH of the reaction solution over a range of from 5 to 6; and
iii) heating the reaction solution to effect the oxidation and cyclization reaction, reacting the reaction product with ammonium chloride or an aqueous solution thereof, and recovering the formed ammonium salt in the form of sparingly soluble crystals.

Though not necessarily limited thereto only, it is considered that the reaction mechanism according to the present invention proceeds as represented by the following formula (6),

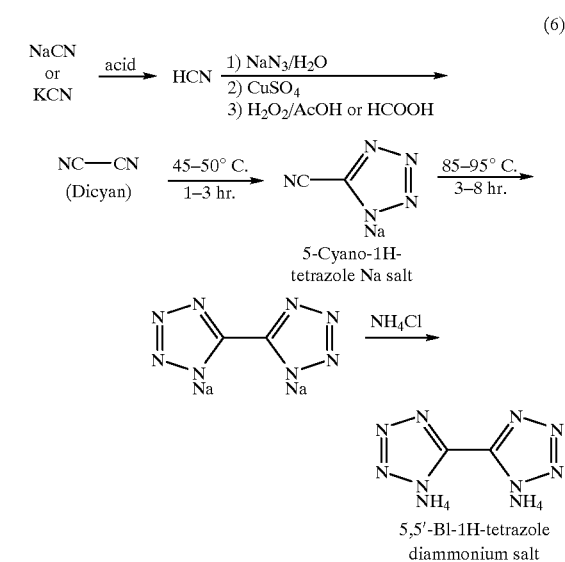

According to the present invention, an aqueous solution of starting materials containing hydrogen cyanide, sodium azide and a catalytic amount of copper sulfate is formed in advance. It is, therefore, considered that these components are homogeneously dispersed, and the reaction proceeds homogeneously over the whole system, preventing the formation of by-products, and contributing to increasing the yields.

It is desired that the starting aqueous solution is prepared at a temperature as low as possible and, generally, at a temperature of not higher than 10° C. to more effectively prevent the occurrence of side reaction and to prevent the leakage of hydrogen cyanide.

According to this process, it is also important to dropwisely add the aqueous hydrogen peroxide to which a small amount of weakly acidic substance has been added, to the starting aqueous solution to maintain the pH of the reaction solution over a range of from 5 to 6. Hydrogen cyanide includes a C≡N triple bond and invites polymerization and many other reactions. According to the present invention, hydrogen peroxide is added simultaneously with the addition of the weakly acidic substance, and the pH of the reaction solution is maintained to lie over the above-mentioned range, in order to enhance the yield and purity by suppressing the side reactions.

According to the reaction of the present invention as represented by the above-mentioned formula (6), the 5,5'-bi-1H-tetrazole disodium salt (BHT.2Na) is formed through cyclization due to the reaction of sodium azide with hydrogen cyanide dimerized by the oxidation. In general, these reactions proceed successively. These reactions, however, may proceed simultaneously.

In the present invention, the 5,5'-bi-1H-tetrazole disodium salt (BHT.2Na) that is formed is reacted with ammonium chloride in the reaction system. This makes it possible to prepare the 5,5'-bi-1H-tetrazole diammonium salt (BHT.2NH$_3$) maintaining a high yield and a high purity.

That is, in contrast with the 5,5'-bi-1H-tetrazole and the 5,5'-bi-1H-tetrazole disodium salt which are soluble in water, the 5,5'-bi-1H-tetrazole diammonium salt which is sparingly soluble in water can be isolated through a simple operation of subjecting the precipitated crystals of after the reaction to the filtration or to the centrifuge.

There is no particular limitation on the method of preparing the starting aqueous solution used in the present invention so far as it has the above-mentioned composition. Described below are the preferred preparation methods to which only, however, the invention is in no way limited.

(1) An aqueous solution of sodium azide is added to an aqueous solution of hydrogen cyanide under the cooled condition and, then, a catalytic amount of copper sulfate is added thereto to prepare a starting aqueous solution (see Examples 1 to 3). This method is excellent concerning the purity and yield of the product.

(2) Alkali cyanide is neutralized with an equivalent amount of acid, an aqueous solution of sodium azide is added to the obtained aqueous solution under the cooled condition and, then, a catalytic amount of copper sulfate is added thereto to prepare a starting aqueous solution (see Examples 4 to 9). As the acid, there are used mineral acids such as hydrochloric acid and the like acid. As the alkali cyanide, there is used sodium cyanide or potassium cyanide. This method offers such an advantage that the starting cyan is easily available and is easy to handle.

(3) To a system containing alkali cyanide, sodium azide and water, there is added an equivalent amount of acid with respect to the alkali cyanide under the cooled condition. To the obtained aqueous solution is then added a catalytic amount of copper sulfate to prepare a starting aqueous solution (see Example 10). This method offers advantages like the method (2).

(4) To a system containing alkali cyanide, sodium azide, catalytic amount of copper sulfate and water, there is added an equivalent amount of acid with respect to the alkali cyanide under the cooled condition to prepare a starting aqueous solution (see Example 11). This method offers advantages like the method (2).

In any one of the above-mentioned methods, it is desired to maintain the temperature of the system over a range of from 0 to 10° C. and, particularly, from 0 to 5° C.

In these methods, furthermore, it is desired to so prepare the starting aqueous solution that the molar ratio (B/A) of the sodium azide (B) to the hydrogen cyanide or the alkali cyanide (A) is from 1.0 to 1.5 from the standpoint of yield and purity.

In the present invention, the aqueous hydrogen peroxide to which a small amount of weakly acidic substance has been added, is dropwisely added to the starting aqueous solution to maintain the pH of the reaction solution over a range of from 5 to 6.

As the weakly acidic substance, there can be preferably used organic carboxylic acid and, particularly, formic acid or acetic acid.

It is desired to so add the aqueous hydrogen peroxide that the molar ratio (C/A) of the hydrogen peroxide (C) to the hydrogen cyanide or the alkali cyanide (A) is from 0.5 to 1.0 from the standpoint of yield and purity.

The molar ratio of the weakly acidic substance such as acetic acid or formic acid added to the aqueous hydrogen peroxide, gives the above-mentioned pH. Here, it is desired that the molar ratio of acetic acid or formic acid/hydrogen peroxide=0.05 to 0.3.

In the present invention, copper sulfate is used as a catalyst. It is desired that copper sulfate is made present in such an amount that the molar ratio (D/C) of the copper sulfate (D) to the hydrogen peroxide (C) is from 0.001 to 0.1 from the standpoint of yield and purity.

In the present invention, the reaction solution containing the above-mentioned components is heated to effect the dimerization by the oxidation and to effect the cyclization reaction. It is desired that the heating is conducted in two steps at a temperature of from 45 to 55° C. for 1 to 3 hours and at a temperature of from 85 to 105° C. for 4 to 12 hours.

Trace experiment using the liquid chromatography indicates that the reaction in the former step is forming a 5-cyano-1H-tetrazole intermediate product and the reaction in the latter step is converting this intermediate product into a 5,5'-bi-1H-tetrazole.

In the present invention, the reaction product is reacted with the ammonium chloride or an aqueous solution thereof, and the formed ammonium salt is recovered as sparingly soluble crystals.

It is desired that the ammonium chloride is so added that the molar ratio (E/A) of the ammonium chloride (E) to the alkali cyanide (A) is from 1.0 to 1.5.

As the ammonium chloride, there can be used the ammonium chloride in a solid form or in the form of an aqueous solution. When added in the form of an aqueous solution, there is obtained a 5,5'-bi-1H-tetrazole diammonium salt having a good crystalline form compared with when the ammonium chloride of the solid form is added.

In the present invention, it is desired that the ammonium chloride is added to the reaction system to carry out the reaction at a temperature of from room temperature to 100° C. for 1 to 3 hours from the standpoint of forming a 5,5'-bi-1H-tetrazole diammonium salt maintaining a good yield.

The hydrogen cyanide or sodium cyanide or potassium cyanide, sodium azide, hydrogen peroxide, copper sulfate and ammonium chloride used for the reaction of the present invention may be those that are industrially produced. The copper sulfate used as the catalyst will be copper sulfate only, a mixture of copper sulfate and ferric sulfate or hydrates thereof. The molar ratio of ferric sulfate/copper sulfate is from 0.1 to 0.5.

According to the present invention, the step of synthesizing the desired 5,5'-bi-1H-tetrazole diammonium salt from the starting materials can be carried out relying on the one-pot reaction. Moreover, the 5,5'-bi-1H-tetrazole diammonium salt can be provided through a very simple operation of filtering and isolating the precipitated crystals maintaining a yield of as high as 70 to 85%. That is, a one-pot synthesis route is established for synthesizing the desired 5,5'-bi-1H-tetrazole diammonium salt without isolating the intermediate product.

EXAMPLES

The invention will now be concretely described by way of Examples to which only, however, the invention is in no way limited.

The 5,5'-bi-1H-tetrazole, 5-cyano-1H-tetrazole intermediate product and hydrogen azide were analyzed relying on the high performance liquid chromatography, and hydrogen cyanide was analyzed relying on the gas chromatography. The content of the 5,5'-bi-1H-tetrazole diammonium salt in the obtained crystals was found relying on the $HClO_4$ titration (%) and the high performance liquid chromatography (HPLC area %).

Example 1

An aqueous solution of 14.05 g (0.518 mole) of 99.7% hydrogen cyanide and 110.0 g of $H_2O$ was cooled to 0° C., and to which was dropwisely added an aqueous solution of 37.12 g (0.570 mole) of 99.8% sodium azide and 100.0 g of $H_2O$ at a dropping temperature of from −4 to 0° C. over a period of 10 minutes. Next, 0.52 g (0.002 mole) of a 99.5% pentahydrate of copper sulfate (II) was added thereto, followed by the dropwise addition of a mixture solution of 26.87 g (0.280 mole) of 35.5% hydrogen peroxide, 26.0 g of $H_2O$ and 2.69 g (0.052 mole) of 88.5% formic acid at a dropping temperature of from −1 to 5° C. over a period of 45 minutes. The pH of the reaction solution was 5 to 6. After the dropwise addition has been finished, the reaction solution was stirred at room temperature for one hour, and the temperature of the reaction solution was elevated to 30° C. Then, the reaction solution was reacted at 40° C. for 2 hours to synthesize a 5-cyano-1H-tetrazole intermediate product, and was further reacted at 90° C. for 6 hours to convert the 5-cyano-1H-tetrazole intermediate product into a 5,5'-bi-1H-tetrazole. The decreased amount of the 5-cyano-1H-tetrazole intermediate product and the formed amount of the 5,5'-bi-1H-tetrazole were found by the high performance liquid chromatography to trace the reaction. After a 5,5'-bi-1H-tetrazole disodium salt has been synthesized, 30.8 g (0.570 mole) of 99.0% ammonium chloride was added in the solid form to the reaction solution to carry out the reaction at 50° C. for 2 hours. Thereafter, the reaction solution was cooled down to 10° C., stirred for 30 minutes, and the precipitated crystals were filtered and were washed with 50.3 g of cold water to isolate 46.50 g of wet crystals. After dried at 50° C. for 10 hours under a reduced pressure, there were obtained 26.72 g of 5,5'-bi-1H-tetrazole diammonium salt crystals. There remained 0.53% by weight or 2.58 g (0.015 mole) of the 5,5'-bi-1H-tetrazole diammonium salt in 486.37 g of the isolated mother liquor plus washing water.

Analysis of 5,5'-bi-1H-tetrazole diammonium salt crystals: Content: $HClO_4$ titration: 95.37% HPLC area %: 98.89% Yield of crystals: 57.2% [based on hydrogen cyanide], 51.9% [based on sodium azide]

Example 2

An aqueous solution of 13.60 g (0.502 mole) of 99.7% hydrogen cyanide and 110.0 g of $H_2O$ was cooled to 0° C., and to which was dropwisely added an aqueous solution of 35.98 g (0.552 mole) of 99.8% sodium azide and 100.0 g of $H_2O$ at a dropping temperature of from 0 to 5° C. over a period of 10 minutes. Next, 0.50 g (0.002 mole) of a 99.5% pentahydrate of copper sulfate (II) was added thereto, followed by the dropwise addition of a mixture solution of 25.60 g (0.271 mole) of 35.5% hydrogen peroxide, 25.1 g of $H_2O$ and 3.04 g (0.050 mole) of 99% acetic acid at a dropping temperature of from 2 to 7° C. over a period of one hour. The pH of the reaction solution was 5 to 6. After the dropwise addition has been finished, the reaction solution was stirred at room temperature for one hour, and the temperature of the reaction solution was elevated to 35° C. Then, the reaction solution was reacted at 40° C. for 2 hours to synthesize a 5-cyano-1H-tetrazole intermediate product, and was further reacted at 90° C. for 6 hours to convert the 5-cyano-1H-tetrazole intermediate product into a 5,5'-bi-1H-tetrazole. After a 5,5'-bi-1H-tetrazole disodium salt has been synthesized, an aqueous solution of 29.84 g (0.552 mole) of 99.0% ammonium chloride and 70.0 g of $H_2O$ was added to the reaction solution at a dropping temperature of 80° C. over a period of one hour. Thereafter, the reaction solution was cooled from 80° C. down to 7° C. over a period of 2.5 hours, so that the crystals were precipitated. The precipitated crystals were filtered and were washed with 50.0 g of cold water to isolate 46.55 g of wet crystals. Since ammonium chloride was dropwisely added in the form of an aqueous solution to the reaction solution, the crystals were favorably separated compared with Example 1. After dried at 50° C. for 5 hours under a reduced pressure, there were obtained 29.21 g of 5,5'-bi-1H-tetrazole diammonium salt crystals. There remained 0.33% by weight or 1.36 g (0.008 mole) of the 5,5'-bi-1H-tetrazole diammonium salt in 411.22 g of the isolated mother liquor plus washing water.

Analysis of 5,5'-bi-1H-tetrazole diammonium salt crystals: Content: $HClO_4$ titration: 98.24% HPLC area %: 99.79% Yield of crystals: 66.4% [based on hydrogen cyanide], 60.4% [based on sodium azide]

Example 3

An aqueous solution of 27.05 g (0.998 mole) of 99.7% hydrogen cyanide and 210.0 g of $H_2O$ was cooled to 0° C., and to which was dropwisely added an aqueous solution of 78.07 g (1.197 mole) of 99.7% sodium azide and 190.0 g of $H_2O$ at a dropping temperature of from −1 to 7° C. over a period of 10 minutes. Next, 2.50 g (0.010 mole) of a 99.5% pentahydrate of copper sulfate (II) was added thereto, followed by the dropwise addition of a mixture solution of 51.87 g (0.539 mole) of 35.3% hydrogen peroxide, 50.0 g of $H_2O$ and 6.00 g (0.100 mole) of 99% acetic acid at a dropping temperature of from 3 to 17° C. over a period of 45 minutes. The pH of the reaction solution was 5 to 6. After the dropwise addition has been finished, the reaction solution was stirred at room temperature for one hour, and the temperature of the reaction solution was elevated to 40° C. Then, the reaction solution was reacted at 40° C. for 2 hours to synthesize a 5-cyano-1H-tetrazole intermediate product, and was further reacted at 90° C. for 2 hours and, then, 4 hours under the heated condition with refluxing to convert the 5-cyano-1H-tetrazole intermediate product into a 5,5'-bi-1H-tetrazole. After a 5,5'-bi-1H-tetrazole disodium salt has been synthesized, an aqueous solution of 64.69 g (1.197 mole) of 99.0% ammonium chloride and 180.0 g of $H_2O$ was dropwisely added to the reaction solution at a dropping temperature of 80° C. over a period of 45 minutes. Thereafter, the reaction solution was cooled from 80° C. down to 7° C. over a period of 2.0 hours to precipitate the crystals. The precipitated crystals were filtered and were washed with 100.0 g of cold water to isolate 96.56 g of wet crystals. After dried at 50° C. for 5 hours under a reduced pressure, there were obtained 73.26 g of 5,5'-bi-1H-tetrazole diammonium salt crystals. There remained 0.25% by weight or 2.14 g (0.012 mole) of the 5,5'-bi-1H-tetrazole diammonium salt in 854.23 g of the isolated mother liquor plus washing water.

Analysis of 5,5'-bi-1H-tetrazole diammonium salt crystals: Content: $HClO_4$ titration: 98.05% HPLC area %: 99.37% Yield of crystals: 84.2% [based on hydrogen cyanide], 70.2% [based on sodium azide]

Example 4

An aqueous solution of 50.91 g (1.00 mole) of 96.4% sodium cyanide and 230.0 g of $H_2O$ was cooled to be not higher than 10° C., and was neutralized by the dropwise addition of 106.0 g (1.00 mole) of 34.4% hydrochloric acid at a dropping temperature of from 3 to 7° C. over a period of 30 minutes. Thereafter, an aqueous solution of 71.73 g (1.10 moles) of 99.8% sodium azide and 180.1 g of $H_2O$ was dropwisely added thereto at a dropping temperature of from 4 to 7° C. over a period of 10 minutes. Next, 1.00 g (0.004 mole) of a 99.5% pentahydrate of copper sulfate (II) was added thereto, followed by the dropwise addition of a mixture solution of 51.72 g (0.54 mole) of 35.5% hydrogen peroxide, 50.04 g of $H_2O$ and 6.01 g (0.10 mole) of 99% acetic acid at a dropping temperature of from 3 to 10° C. over a period of 40 minutes. The pH of the reaction solution was 5 to 6. After the dropwise addition has been finished, the reaction solution was stirred at room temperature for one hour, and the temperature of the reaction solution was elevated to 20° C. Then, the reaction solution was reacted at 40° C. for 2 hours to synthesize a 5-cyano-1H-tetrazole intermediate product, and was further reacted at 90° C. for 6 hours to convert the 5-cyano-1H-tetrazole intermediate product into a 5,5'-bi- 1H-tetrazole. After a 5,5'-bi-1H-tetrazole disodium salt has been synthesized, an aqueous solution of 59.49 g (1.10 moles) of 99.0% ammonium chloride and 158.9 g of $H_2O$ was added to the reaction solution at a dropping temperature of 80° C. over a period of 1.25 hours. Thereafter, the reaction solution was cooled from 80° C. down to 9° C. over a period of 2.5 hours to precipitate the crystals. The precipitated crystals were filtered and were washed with 99.7 g of cold water to isolate 102.7 g of wet crystals. After dried at 50° C. for 10 hours under a reduced pressure, there were obtained 56.53 g of 5,5'-bi-1H-tetrazole diammonium salt crystals. There remained 0.27% by weight or 2.57 g (0.015 molr) of the 5,5'-bi-1H-tetrazole diammonium salt in 948.87 g of the isolated mother liquor plus washing water.

Analysis of 5,5'-bi-1H-tetrazole diammonium salt crystals: Content: $HClO_4$ titration: 95.88% HPLC area %: 99.72% Yield of crystals: 62.9% [based on sodium cyanide], 57.2% [based on sodium azide]

Example 5

An aqueous solution of 50.82 g (1.00 mole) of 96.4% sodium cyanide and 230.0 g of $H_2O$ was cooled to be not higher than 10° C., and was neutralized by the dropwise addition of 105.8 g (1.00 mole) of 34.4% hydrochloric acid at a dropping temperature of from 3 to 12° C. over a period of 25 minutes. Thereafter, an aqueous solution of 71.71 g (1.10 moles) of 99.8% sodium azide and 181.3 g of $H_2O$ was dropwisely added thereto at a dropping temperature of from 5 to 7° C. over a period of 15 minutes. Next, 1.00 g (0.004 mole) of a 99.5% pentahydrate of copper sulfate (II) was added thereto, followed by the dropwise addition of a mixture solution of 51.85 g (0.54 mole) of 35.5% hydrogen peroxide, 50.04 g of $H_2O$ and 6.01 g (0.10 mole) of 99% acetic acid at a dropping temperature of from 3 to 10° C. over a period of 30 minutes. After the dropwise addition has been finished, the reaction solution was stirred at room temperature for one hour, and the temperature of the reaction solution was elevated to 29° C. Then, the reaction solution was cooled again, and to which was dropwisely added a mixture solution of 25.93 g (0.27 mole) of 35.5% hydrogen peroxide, 25.02 g of $H_2O$ and 3.00 g (0.05 mole) of 99% acetic acid at a dropping temperature of from 4 to 8° C. over a period of 30 minutes. The pH of the reaction solution was from 5 to 6. After the dropwise addition has been finished, the reaction solution was stirred at room temperature for one hour, and the temperature of the reaction solution was elevated to 19° C. Then, the reaction solution was reacted at 40° C. for 2 hours to synthesize a 5-cyano-1H-tetrazole intermediate product, and was further reacted at 90° C. for 6 hours to convert the 5-cyano-1H-tetrazole intermediate product into a 5,5'-bi-1H-tetrazole. After a 5,5'-bi-1H-tetrazole disodium salt has been synthesized, an aqueous solution of 59.45 g (1.10 moles) of 99.0% ammonium chloride and 158.9 g of $H_2O$ was added to the reaction solution at a dropping temperature of 80° C. over a period of 1.25 hours. Thereafter, the reaction solution was cooled from 80° C. down to 8° C. over a period of 2.0 hours to precipitate the crystals. The precipitated crystals were filtered and were washed with 100.2 g of cold water to isolate 91.66 g of wet crystals. After dried at 50° C. for 10 hours under a reduced pressure, there were obtained 60.21 g of 5,5'-bi-1H-tetrazole diammonium salt crystals. There remained 0.24% by weight or 2.43 g (0.014 mole) of the 5,5'-bi-1H-tetrazole diammonium salt in 1013.1 g of the isolated mother liquor plus washing water.

Analysis of 5,5'-bi-1H-tetrazole diammonium salt crystals: Content: $HClO_4$ titration: 96.75% HPLC area %: 98.15% Yield of crystals: 67.7% [based on sodium cyanide], 61.5% [based on sodium azide]

Example 6

An aqueous solution of 50.84 g (1.00 mole) of 96.4% sodium cyanide and 230.0 g of $H_2O$ was cooled to be not higher than 10° C., and was neutralized by the dropwise addition of 105.8 g (1.00 mole) of 34.4% hydrochloric acid at a dropping temperature of from 3 to 10° C. over a period of 30 minutes. Thereafter, an aqueous solution of 71.67 g (1.10 moles) of 99.8% sodium azide and 180.0 g of $H_2O$ was dropwisely added thereto at a dropping temperature of from 4 to 7° C. over a period of 15 minutes. Next, 1.00 g (0.004 mole) of a 99.5% pentahydrate of copper sulfate (II) was added thereto, followed by the dropwise addition of a mixture solution of 51.85 g (0.54 mole) of 35.5% hydrogen peroxide, 50.00 g of $H_2O$ and 6.12 g (0.10 mole) of 99% acetic acid at a dropping temperature of from 3 to 9° C. over a period of 30 minutes. After the dropwise addition has been finished, the reaction solution was stirred at room temperature for one hour, and the temperature of the reaction solution was elevated to 28° C. Then, the reaction solution was reacted at 40° C. for 2 hours to synthesize a 5-cyano-1H-tetrazole intermediate product, and was further reacted at 90° C. for 12 hours to convert the 5-cyano-1H-tetrazole intermediate product into a 5,5'-bi-1H-tetrazole. After a 5,5'-bi-1H-tetrazole disodium salt has been synthesized, an aqueous solution of 59.43 g (1.10 moles) of 99.0% ammonium chloride and 160.00 g of $H_2O$ was added to the reaction solution at a dropping temperature of 80° C. over a period of 1.0 hour. Thereafter, the reaction solution was cooled from 80° C. down to 10° C. over a period of 2.0 hours to precipitate the crystals. The precipitated crystals were filtered and were washed with 100.0 g of cold water to isolate 94.93 g of wet crystals. After dried at 50° C. for 10 hours under a reduced pressure, there were obtained 64.23 g of 5,5'-bi-1H-tetrazole diammonium salt crystals. There remained 0.34% by weight or 3.27 g (0.019 mole) of the 5,5'-bi-1H-tetrazole diammonium salt in 960.01 g of the isolated mother liquor plus washing water.

Analysis of 5,5'-bi-1H-tetrazole diammonium salt crystals: Content: $HClO_4$ titration: 97.12% HPLC area %: 99.77% Yield of crystals: 72.5% [based on sodium cyanide], 66.0% [based on sodium azide]

Example 7

An aqueous solution of 50.85 g (1.00 mole) of 96.4% sodium cyanide and 230.1 g of $H_2O$ was cooled to be not higher than 10° C., and was neutralized by the dropwise addition of 106.1 g (1.00 mole) of 34.4% hydrochloric acid at a dropping temperature of from 2 to 8° C. over a period of 30 minutes. Thereafter, an aqueous solution of 71.73 g (1.10 moles) of 99.7% sodium azide and 180.1 g of $H_2O$ was dropwisely added thereto at a dropping temperature of from 1 to 4° C. over a period of 15 minutes. Next, 1.00 g (0.004 mole) of a 99.5% pentahydrate of copper sulfate (II) was added thereto, followed by the dropwise addition of a mixture solution of 51.78 g (0.54 mole) of 35.5% hydrogen peroxide, 50.08 g of $H_2O$ and 6.00 g (0.10 mole) of 99% acetic acid at a dropping temperature of from 2 to 10° C. over a period of 70 minutes. After the dropwise addition has been finished, the reaction solution was stirred at room temperature for one hour, and the temperature of the reaction solution was elevated to 33° C. Then, the reaction solution was reacted at 40° C. for 2 hours to synthesize a 5-cyano-1H-tetrazole intermediate product, and was further reacted at 90° C. for 2 hours and, then, for another 5 hours under the heated condition with refluxing to convert the 5-cyano-1H-tetrazole intermediate product into a 5,5'-bi-1H-tetrazole. After a 5,5'-bi-1H-tetrazole disodium salt has been synthesized, an aqueous solution of 59.43 g (1.10 moles) of 99.0% ammonium chloride and 160.00 g of $H_2O$ was added to the reaction solution at a dropping temperature of 80° C. over a period of 40 minutes. Thereafter, the reaction solution was cooled from 80° C. down to 10° C. over a period of 2.0 hours to precipitate the crystals. The precipitated crystals were filtered and were washed with 100.0 g of cold water to isolate 96.12 g of wet crystals. After dried at 50° C. for 10 hours under a reduced pressure, there were obtained 65.99 g of 5,5'-bi-1H-tetrazole diammonium salt crystals. There remained 0.32% by weight or 3.10 g (0.018 mole) of the 5,5'-bi-1H-tetrazole diammonium salt in 950.26 g of the isolated mother liquor plus washing water.

Analysis of 5,5'-bi-1H-tetrazole diammonium salt crystals: Content: $HClO_4$ titration: 96.11% HPLC area %: 99.65% Yield of crystals: 73.7% [based on sodium cyanide], 67.0% [based on sodium azide]

Example 8

An aqueous solution of 50.85 g (1.00 mole) of 96.4% sodium cyanide and 230.1 g of $H_2O$ was cooled to be not higher than 10° C., and was neutralized by the dropwise addition of 106.2 g (1.00 mole) of 34.4% hydrochloric acid at a dropping temperature of from 3 to 8° C. over a period of 30 minutes. Thereafter, an aqueous solution of 71.67 g (1.10 moles) of 99.8% sodium azide and 180.1 g of $H_2O$ was dropwisely added thereto at a dropping temperature of from 1 to 4° C. over a period of 15 minutes. Next, 2.51 g (0.010 mole) of a 99.5% pentahydrate of copper sulfate (II) was added thereto, followed by the dropwise addition of a mixture solution of 51.86 g (0.54 mole) of 35.5% hydrogen peroxide, 50.14 g of $H_2O$ and 6.10 g (0.10 mole) of 99% acetic acid at a dropping temperature of from 3 to 10° C. over a period of one hour. After the dropwise addition has been finished, the reaction solution was stirred at room temperature for one hour, and the temperature of the reaction solution was elevated to 28° C. Then, the reaction solution was reacted at 40° C. for 2 hours to synthesize a 5-cyano-1H-tetrazole intermediate product, and was further reacted at 90° C. for 6 hours to convert the 5-cyano-1H-tetrazole intermediate product into a 5,5'-bi-1H-tetrazole. After a 5,5'-bi-1H-tetrazole disodium salt has been synthesized, an aqueous solution of 59.52 g (1.10 moles) of 99.0% ammonium chloride and 160.00 g of $H_2O$ was dropwisely added to the reaction solution at a dropping temperature of 80° C. over a period of one hour. Thereafter, the reaction solution was cooled from 80° C. down to 6° C. over a period of 2.5 hours to precipitate the crystals. The precipitated crystals were filtered and were washed with 99.8 g of cold water to isolate 103.5 g of wet crystals. After dried at 50° C. for 9 hours under a reduced pressure, there were obtained 65.33 g of 5,5'-bi-1H-tetrazole diammonium salt crystals. There remained 0.38% by weight or 3.63 g (0.021 mole) of the 5,5'-bi-1H-tetrazole diammonium salt in 955.57 g of the isolated mother liquor plus washing water.

Analysis of 5,5'-bi-1H-tetrazole diammonium salt crystals: Content: $HClO_4$ titration: 97.15% HPLC area %: 99.36% Yield of crystals: 73.7% [based on sodium cyanide], 67.1% [based on sodium azide]

Example 9

An aqueous solution of 50.86 g (1.00 mole) of 96.4% sodium cyanide and 230.0 g of $H_2O$ was cooled to be not higher than 10° C., and was neutralized by the dropwise addition of 106.1 g (1.00 mole) of 34.4% hydrochloric acid at a dropping temperature of from 2 to 8° C. over a period of 30 minutes. Thereafter, an aqueous solution of 71.78 g (1.10 moles) of 99.7% sodium azide and 180.0 g of $H_2O$ was dropwisely added thereto at a dropping temperature of from 1 to 5° C. over a period of 15 minutes. Next, 2.50 g (0.010 mole) of a 99.5% pentahydrate of copper sulfate (II) was added thereto, followed by the dropwise addition of a mixture solution of 52.05 g (0.54 mole) of 35.5% hydrogen peroxide, 50.01 g of $H_2O$ and 6.04 g (0.10 mole) of 99% acetic acid at a dropping temperature of from 3 to 9° C. over a period of one hour. After the dropwise addition has been finished, the reaction solution was stirred at room temperature for one hour, and the temperature of the reaction solution was elevated to 30° C. Then, the reaction solution was reacted at 40° C. for 2 hours to synthesize a 5-cyano-1H-tetrazole intermediate product, and was further reacted at 90° C. for 2 hours and for another 5 hours under the heated condition with refluxing to convert the 5-cyano-1H-tetrazole intermediate product into a 5,5'-bi-1H-tetrazole. After a 5,5'-bi-1H-tetrazole disodium salt has been synthesized, an aqueous solution of 59.43 g (1.10 moles) of 99.0% ammonium chloride and 159.70 g of $H_2O$ was added to the reaction solution at a dropping temperature of 80° C. over a period of one hour. Thereafter, the reaction solution was cooled from 80° C. down to 10° C. over a period of 2.0 hours to precipitate the crystals. The precipitated crystals were filtered and were washed with 100.0 g of cold water to isolate 119.5 g of wet crystals. After dried at 50° C. for 9 hours under a reduced pressure, there were obtained 71.21 g of 5,5'-bi-1H-tetrazole diammonium salt crystals. There remained 0.38% by weight or 3.08 g (0.018 mole) of the 5,5'-bi-1H-tetrazole diammonium salt in 935.25 g of the isolated mother liquor plus washing water.

Analysis of 5,5'-bi-1H-tetrazole diammonium salt crystals: Content: $HClO_4$ titration: 96.7% HPLC area %: 100.00% Yield of crystals: 80.0% [based on sodium cyanide], 72.7% [based on sodium azide]

Example 10

101.68 Grams (2.00 moles) of 96.4% sodium cyanide, 143.46 g (2.20 moles) of 99.8% sodium azide and 460.17 g of $H_2O$ were simultaneously fed into a 2-liter flask, cooled to be not higher than 10° C., and were neutralized by the dropwise addition of 204.9 g (2.00 moles) of 35.6% hydrochloric acid equivalent to the sodium cyanide at a dropping temperature of from 5 to 9° C. over a period of 55 minutes. Thereafter, a mixture solution of 5.01 g (0.020 mole) of a 99.5% pentahydrate of copper sulfate (II) and 20.07 g of $H_2O$ was dropwisely added thereto at a dropping temperature of from −2 to 2° C. over a period of 5 minutes. Next, a mixture solution of 106.10 g (1.08 moles) of 34.6% hydrogen peroxide and 12.09 g (0.20 mole) of 99% acetic acid was added thereto at a dropping temperature of from −4 to 12° C. over a period of 1.5 hours. After the dropwise addition has been finished, the reaction solution was stirred at room temperature for one hour, and the temperature of the reaction solution was elevated to 40° C. Then, the reaction solution was reacted at 40° C. for 2 hours to synthesize a 5-cyano-1H-tetrazole intermediate product, and was further reacted at 90° C. for 2 hours and for another 5 hours under the heated condition with refluxing to convert the 5-cyano-1H-tetrazole intermediate product into a 5,5'-bi-1H-tetrazole. After a 5,5'-bi-1H-tetrazole disodium salt has been synthesized, an aqueous solution of 118.9 g (2.20 moles) of 99.0% ammonium chloride and 328.3 g of $H_2O$ was added to the reaction solution at a dropping temperature of 80° C. over a period of 1.8 hours. Thereafter, the reaction solution was cooled from 80° C. down to 10° C. over a period of 2.0 hours to precipitate the crystals. The precipitated crystals were filtered and were washed with 199.6 g of cold water to isolate 173.28 g of wet crystals. After dried at 50° C. for 10 hours under a reduced pressure, there were obtained 142.04 g of 5,5'-bi-1H-tetrazole diammonium salt crystals.

Analysis of 5,5'-bi-1H-tetrazole diammonium salt crystals: Content: $HClO_4$ titration: 96.96% HPLC area %: 99.68% Yield of crystals: 80.0% [based on sodium cyanide], 72.7% [based on sodium azide]

Example 11

50.89 Grams (1.00 mole) of 96.4% sodium cyanide, 71.78 g (1.10 moles) of 99.8% sodium azide and 230.0 g of $H_2O$ were simultaneously fed into a 1-liter flask, cooled to be not higher than 10° C., and were neutralized by the dropwise addition of 102.0 g (1.00 mole) of 35.8% hydrochloric acid equivalent to the sodium cyanide at a dropping temperature of from 2 to 8° C. over a period of 30 minutes. Thereafter, a mixture solution of 2.50 g (0.010 mole) of a 99.5% pentahydrate of copper sulfate (II) and 10.45 g of $H_2O$ was dropwisely added thereto at a dropping temperature of from 2 to 3° C. over a period of 2 minutes. Next, a mixture solution of 53.13 g (0.54 mole) of 34.6% hydrogen peroxide and 6.02 g (0.10 mole) of 99% acetic acid was added thereto at a dropping temperature of from 3 to 20° C. over a period of 45 minutes. After the dropwise addition has been finished, the reaction solution was stirred at room temperature for one hour, and the temperature of the reaction solution was elevated to 40° C. Then, the reaction solution was reacted at 40° C. for 2 hours to synthesize a 5-cyano-1H-tetrazole intermediate product, and was further reacted at 90° C. for 2 hours and for another 5 hours under the heated condition with refluxing to convert the 5-cyano-1H-tetrazole intermediate product into a 5,5'-bi-1H-tetrazole. After a 5,5'-bi-1H-tetrazole disodium salt has been synthesized, an aqueous solution of 59.40 g (1.10 moles) of 99.0% ammonium chloride and 160.7 g of $H_2O$ was added to the reaction solution at a dropping temperature of 80° C. over a period of one hour. Thereafter, the reaction solution was cooled from 80° C. down to 8° C. over a period of 2.0 hours to precipitate the crystals. The precipitated crystals were filtered and were washed with 100.1 g of cold water to isolate 98.23 g of wet crystals. After dried at 50° C. for 10 hours under a reduced pressure, there were obtained 65.83 g of 5,5'-bi-1H-tetrazole diammonium salt crystals.

Analysis of 5,5'-bi-1H-tetrazole diammonium salt crystals: Content: $HClO_4$ titration: 97.53% HPLC area %: 99.15% Yield of crystals: 74.0% [based on sodium cyanide], 67.3% [based on sodium azide]

Reference Example 1
[Synthesis of 5,5'-bi-1H-tetrazole disodium salt]

An aqueous solution of 26.70 g (0.985 mole) of 99.7% hydrogen cyanide and 210.0 g of $H_2O$ was cooled to 0° C., and to which was dropwisely added an aqueous solution of 69.04 g (1.059 moles) of 99.7% sodium azide and 170.0 g of $H_2O$ at a dropping temperature of from 2 to 9° C. over a period of 10 minutes. Next, 0.99 g (0.004 mole) of a 99.5% pentahydrate of copper sulfate (II) was added thereto, followed by the dropwise addition of a mixture solution of 51.21 g (0.532 mole) of 35.5% hydrogen peroxide, 50.0 g of $H_2O$ and 5.12 g (0.098 mole) of 88.5% formic acid at a dropping temperature of from 3 to 8° C. over a period of 45 minutes. The pH of the reaction solution was 5 to 6. After the dropwise addition has been finished, the reaction solution was stirred at room temperature for one hour, and the temperature of the reaction solution was elevated to 30° C. Then, the reaction solution was reacted at 40 to 45° C. for one hour to synthesize a 5-cyano-1H-tetrazole intermediate product, and was further reacted at 90 to 95° C. for one hour and for another two hours under the heated condition with refluxing to convert the 5-cyano-1H-tetrazole intermediate product into a 5,5'-bi-1H-tetrazole. However, the 5-cyano-1H-tetrazole intermediate product remained in the reaction solution. The reaction solution was then condensed under a reduced pressure, and was cooled down to 10° C. to isolate wet crystals. After dried at 50° C. for 10 hours under a reduced pressure, there were obtained 28.70 g of 5,5'-bi-1H-tetrazole disodium salt crystals, yield, 32.0%.

What is claimed is:

1. A process for the preparation of 5,5'-bi- 1H tetrazole diammonium salt by dropwise adding aqueous hydrogen peroxide having an amount of acetic acid or formic acid to maintain the pH of the reaction solution over a range of from 5 to 6, to a starting aqueous solution of hydrogen cyanide or alkali cyanide, sodium azide and a catalytic amount of copper sulfate, heating the reaction solution to effect an oxidation and cyclization reaction, reacting the reaction product with ammonium chloride or an aqueous solution thereof, and recovering the formed ammonium salt in the form of crystals.

2. A process according to claim 1, wherein the starting aqueous solution is obtained by adding an aqueous solution of sodium azide to an aqueous solution of the hydrogen cyanide at a temperature of not higher than 10° C. and, then, adding a catalytic amount of copper sulfate thereto.

3. A process according to claim 1, wherein the starting aqueous solution is obtained by neutralizing an alkali cyanide with equivalent amount of an acid at a temperature of not higher than 10° C. and, adding a catalytic amount of copper sulfate thereto.

4. A process according to claim 1, wherein the starting aqueous solution is obtained by adding an acid to a system that contains alkali cyanide, sodium azide and water at a temperature of not higher than 10° C., said acid being added in an amount equivalent to the amount of the alkali cyanide, and then, adding a catalytic amount of copper sulfate thereto.

5. A process according to claim 1, wherein the starting aqueous solution is obtained by adding an acid to a system that contains alkali cyanide, sodium azide, a catalytic amount of copper sulfate and water at a temperature of not higher than 10° C., said acid being added in an amount equivalent to the amount of the alkali cyanide.

6. A process according to claim 1, wherein the starting aqueous solution is so prepared that the molar ratio (B/A) of the sodium azide (B) to the hydrogen cyanide or the alkali cyanide (A) is from 1.0 to 1.5.

7. A process according to claim 1, wherein the aqueous hydrogen peroxide is so added that the molar ratio (C/A) of the hydrogen peroxide (C) to the hydrogen cyanide or the alkali cyanide (A) is from 0.5 to 1.0.

8. A process according to claim 1, wherein copper sulfate is made present so that the molar ratio (D/C) of the copper sulfate (D) to the hydrogen peroxide (C) is from 0.001 to 0.1.

9. A process according to claim 1, wherein the reaction solution is heated in two steps at a temperature of from 45 to 55° C. for 1 to 3 hours and, then, at a temperature of from 85 to 105° C. for 4 to 12 hours.

10. A process according to claim 1, wherein the ammonium chloride is so added that the molar ratio (E/A) of the ammonium chloride (E) to the hydrogen cyanide or the alkali cyanide (A) is from 1.0 to 1.5.

11. A process according to claim 1, wherein the ammonium chloride is added to carry out the reaction at room temperature to 100° C. for 1 to 3 hours.

12. A process according to claim 1, wherein the acetic acid or the formic acid is added to the aqueous hydrogen peroxide at such a molar ratio that acetic acid or formic acid/hydrogen peroxide=0.05 to 0.3.

* * * * *